United States Patent [19]

Duggan et al.

[11] Patent Number: 4,618,729
[45] Date of Patent: Oct. 21, 1986

[54] RUTHENIUM-COBALT CARBONYL METAL CLUSTER CATALYSTS FOR THE DEALKOXYHYDROXYMETHYLATION OF ACETALS TO FORM GLYCOL ETHERS

[75] Inventors: D. Michael Duggan, Drexel Hill; James E. Lyons, Wallingford; Harry K. Myers, Jr., Cochranville, all of Pa.

[73] Assignee: Sun Refining and Marketing Company, Philadelphia, Pa.

[21] Appl. No.: 782,807

[22] Filed: Oct. 2, 1985

Related U.S. Application Data

[63] Continuation-in-part of Ser. No. 622,816, Jun. 21, 1984, abandoned.

[51] Int. Cl.$^4$ .................. C07C 41/28; C07C 41/18
[52] U.S. Cl. ..................... 568/678; 568/648; 568/664; 568/665; 568/670; 568/649
[58] Field of Search ............... 568/648, 678, 670, 664, 568/649, 665

[56] References Cited

U.S. PATENT DOCUMENTS

| | | | |
|---|---|---|---|
| 4,062,898 | 12/1977 | Dubeck et al. | 568/678 X |
| 4,079,085 | 3/1978 | Wall | 568/678 |
| 4,357,477 | 11/1982 | Knifton | 568/678 |
| 4,390,734 | 6/1983 | Knifton | 568/678 |

Primary Examiner—Bernard Helfin
Attorney, Agent, or Firm—J. Edward Hess; Donald R. Johnson; Stanford M. Back

[57] ABSTRACT

The ruthenium-cobalt carbonyl metal cluster catalyst $Co_2Ru(CO)_{11}$ effectively catalyzes the dealkoxyhydroxymethylation of aldehyde acetals to form glycol monoethers. Methylal, for example, may be reacted with syngas, i.e., CO and $H_2$, in the presence of this ruthenium-cobalt cluster catalyst to form the monomethyl ether of ethylene glycol.

16 Claims, No Drawings

RUTHENIUM-COBALT CARBONYL METAL CLUSTER CATALYSTS FOR THE DEALKOXYHYDROXYMETHYLATION OF ACETALS TO FORM GLYCOL ETHERS

CROSS-REFERENCE TO RELATED APPLICATION

This application is a continuation-in-part of Ser. No. 622,816, filed June 21, 1984 and now abandoned.

BACKGROUND OF THE INVENTION

1. Scope of the Invention

This invention relates to the dealkoxyhydroxymethylation of aldehyde acetals. More particularly, it relates to a novel process for the dealkoxyhydroxymethylation of certain dialkyl-, dicycloalkyl-, diaryl-, or cyclic-aldehyde acetals by reacting said acetals with syngas, i.e., hydrogen and carbon monoxide, in the presence of a catalyst comprising a ruthenium-cobalt carbonyl metal cluster to form the corresponding glycol monoethers. The acetals described herein may be prepared separately or formed in situ from the corDesponding aldehyde and alcohol precursors.

The glycol ethers described herein encompass known classes of compounds having various uses, as for example as jet fuel additives, cleaners, coatings solvents, intermediates in the production of certain diphthalates, and the like.

2. Description of the Prior Art

One current well-known method of manufacturing glycol monoethers such as monoalkyl ethers consists of reacting ethylene oxide with the alcohol corresponding to the desired alkyl ether, employing various known catalyst systems.

Alternatively, the cobalt-catalyzed reaction of aldehydes or their dialkyl acetals with syngas, i.e., a carbon monoxide-hydrogen mixture, to form the corresponding glycol ether is also described in the art. Thus, for example, a method of making ethylene glycol ethers is described in U.S. Pat. No. 2,525,793 which employs cobalt oxide to catalyze the reaction of methylal with syngas to provide a reaction mixture which, after hydrogenation over nickel, gives relatively uneconomical conversions on the order of 25–33%.

Numerous attempts have been made to obtain more practical yields of glycol ethers from aldehydes or their dialkylacetals. A number of promoters have been used in conjunction with various cobalt catalysts in an effort to improve reaction rates and product yields. U.S. Pat. No. 4,062,898, for example, discloses a ruthenium chloride-promoted cobalt iodide catalyst which hydrocarbonylates formaldehyde dimethylacetal (methylal) to ethylene glycol monomethyl ether, (EGMME) in yields of 10% or less. The reaction temperature required is 185° C. at 20 atm. or above. A second method, described in Jpn. Kokai Tokkyo Koho 81 83,432, (1981) uses substantial quantitites of 2,4,6-collidine or similar aromatic amines to promote the cobalt carbonyl-catalyzed hydrocarbonylation of methylal in benzene as a solvent. The reaction of methylal with highly pressurized syngas in this process at 190° C. for 10 hours gave 44% selectively to EGMME at 98% conversion. A further patent, Euro. Pat. Appln. No. EP 34,374 (1981) uses both iodine and triphenyl or tricyclohexylphosphine together with $RuCl_3 \cdot H_2O$, to promote the $Co(Ac)_2 \cdot 4H_2O$, - catalyzed hydrocarbonylation of methylal using 3000 psig of syngas, and temperatures of between 150° and 175° C. to obtain results nearly comparable to those of the Japanese.

More recently, Knifton has found that cobalt carbonyl promoted with a Group VIB donor ligand catalyzes the hydrocarbonylation of an aldehyde in an alcohol to make ethylene glycol monoethers; U.S. Pat. No. 4,308,403. Yields of ethylene glycol monobutyl ether (EGMBE) as high as 61 wt. % were reported in this patent. A cyclopentadienyl-ligated cobalt catalyst is also effective for these reactions giving glycol ethers in up to 54% yield; U.S. Pat. No. 4,317,943.

Propylene glycol monoalkyl ethers are formed by contacting high pressure mixtures of carbon monoxide and hydrogen with either an acetal or an aldehyde and an alcohol using a cobalt catalyst promoted with a tin- or germanium-containing compound; U.S. Pat. No. 4,356,327. Yields of glycol ethers up to 31 wt. % were reported in this patent. Ethylene glycol ethers were also formed from a formaldehyde acetal or formaldehyde and an alcohol using tin or germanium promoters for cobalt carbonyl; U.S. Pat. No. 4,357,477. The highest glycol ether yield (EGMBE) was 53% in this case.

Further, propylene glycol monoalkyl ethers were formed by hydrocarbonylation of acetaldehyde acetals or acetaldehyde and alcohols using rhodium, ruthenium or nickel compounds to promote either cobalt carbonyls or cobalt compounds having group V ligand systems attached. Glycol ether yields up to 28 wt. % were realized when these promoters were used; Knifton, U.S. Pat. No. 4,390,734 (1983).

Thus, the use of various promoters for the cobalt-catalyzed hydrocarbonylation of aldehydes or acetals has resulted in glycol ether yields of from 10–61 wt. %, depending on the glycol ether produced. The highest reported yield of EGMME is 44%, of EGMBE is 61% and propylene glycol monethyl ether, PGMEE is 28%.

SUMMARY OF THE INVENTION

In accordance with the present invention, there is provided an improved process for the reaction of certain dialkyl-, dicycloalkyl-, diaryl-, or cyclic- aldehyde acetals or their aldehyde-alcohol precursors with syngas in the presence of the ruthenium-cobalt carbonyl catalyst $Co_2Ru(CO)_{11}$, to form the corresponding glycol monoethers. This reaction, which may best be described as the dealkoxyhydroxymethylation of an acetal, formed separately or in situ by the known reaction of an aldehyde with an alcohol, may be depicted by the following general reaction scheme:

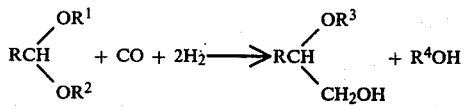

wherein R is hydrogen, alkyl, cycloalkyl, or aryl; $R^1$ and $R^2$, which may be the same or different, are alkyl, cycloalkyl, or aryl, and taken together may form a cyclic acetal; $R^3$ is alkyl, cycloalkyl, aryl, or an hydroxy-substituted hydrocarbon moiety; and $R^4$ is alkyl, cycloalkyl, or aryl corresponding to whichever $R^1$ or $R^2$ group is displaced. In the case where cyclic acetals are employed, however, no alcohol by-product is formed.

Examples of $R^1$, $R^2$, $R^3$ or $R^4$ alkyl, cycloalkyl, and aryl groups which may be employed include such substituted or unsubstituted groups as:

(a) straight or branched chain alkyl groups, preferably those having from 1 to about 20 carbon atoms, such as methyl, ethyl, propyl, isopropyl, n-butyl, t-butyl, 2-ethylhexyl, dodecyl, and the like;

(b) substituted or unsubstituted cycloalkyl groups, preferably those having from about 5 to about 20 carbon atoms, such as cyclopentyl, cyclohexyl, cycloheptyl, 3-methylcyclopentyl, 3-butyl cyclohexyl, cyclooctyl, adamantyl, decalyl, cyclooctyl, 3-phenylcycloheptyl and the like; and (c) substituted or unsubstituted aryl groups, preferably those having from 6 to about 20 carbon atoms such as benzyl, phenyl, naphthyl, fluoranthyl, tetralyl, tolyl, ethylphenyl, cumyl, anisyl, chlorophenyl, and the like.

It will be understood that when $R^1$ and $R^2$ in the foregoing reaction scheme are different, the resulting product will actually be mixtures of the corresponding glycol ethers and alcohols. It will also be understood, as mentioned above, that $R^1$ and $R^2$ may be joined by one or more bridging atoms to form a cyclic acetal, in which case, under the conditions of this reaction the heterocyclic ring will cleave at a carbon-oxygen bond of the acetal moiety, and hydroxymethylate, thereby forming a dihydroxy compound, i.e. an hydroxy-substituted glycol ether.

This process provides an improvement over the methods of the prior art in that the instant catalyst does not require the added presence of the iodide, amines, or phosphine promoters such as are disclosed in the prior art, and thus is less costly and easier to prepare and recover. Moreover, these novel catalysts permit the reaction to be carried out under mild conditions of time and temperature, yet most surprisingly provide rates and selectivities of desired product over those obtained by the use of cobalt carbonyl alone.

DESCRIPTION OF THE PREFERRED EMBODIMENTS

The catalyst of this invention consists of the metal cluster $Co_2Ru(CO)_{11}$. This catalyst may be prepared by the method disclosed by Roland et al., *Angew. Chem. Int. Ed. Engl.*, 20, 679 (1981).

The acetal dealkoxyhydroxymethylation reaction with syngas utilizing the ruthenium-cobalt carbonyl metal cluster catalyst may conveniently be conducted in a generally known manner whereby the desired acetal is reacted with syngas under elevated temperature and pressures for given periods of time, during which period the reaction mixture is actively stirred. In this reaction, the volume ratio of carbon monoxide to hydrogen in the syngas desirably is in the range of from about 1:5 to 5:1, and more preferably 1:3 to 3:1. Following rapid cooling, the reaction product is then recovered from the mixture in a routine manner.

In contrast to prior art reaction conditions described above, the ruthenium-cobalt carbonyl metal cluster, $Co_2Ru(CO)_{11}$, advantageously permits the use of mild operating conditions. Thus, temperatures in the range of from about 100° to 200° C., and preferably about 125° to 175° C., pressures of from about 500 to 5000 psi, and preferably about 1000 to 3000 psi, may satisfactorily be employed. The reaction time is not critical, and may range up to several hours, desirably about 1–4 hours.

The weight ratio, in grams, of catalyst mixture to acetal is desirably in the range of from about 1:1000–10:1, and preferably in the range of from about 1:100–1:1 in a batch reaction.

In a further embodiment of this invention, it has been found that highly advantageous effects may also be obtained in this dealkoxyhydroxymethylation process by the use of solvents with the acetal. The solvents which may be advantageously used comprise any polar or non-polar organic solvents which are inert to the conditions of the reaction. Included amongst these solvents are $C_{1-12}$ alcohols, preferably those corresponding to the alkyl group of the acetal, such as methanol, ethanol, butanol, 3-ethyl-2-hexanol and the like; ethers which will not cleave under the conditions of the reaction, such as glyme, diglyme, diphenyl ether and the like; aromatics and substituted aromatics such as benzene, toluene, xylene, chlorobenzene, dichlorobenzene, anisole, and the like.

The solvents may be employed in amounts of up to 90 volume percent of the reaction mixture, and preferably in amounts of about 20 to 80 percent.

In still a further embodiment of this process, it has been found that with acyclic acetals, when the reaction is carried out in an excess of an alcohol solvent, wherein the ratio of acetal to alcohol solvent is desirably in the range of from about 1:2 to 1:20, and preferably 1:5 to 1:10, and wherein the R group of the alcohol used is different from the $R^1$ and/or $R^2$ substituents on the acetal starting material, these different R groups of the alcohol will, in the course of the reaction, replace the $R^1$ and/or $R^2$ groups on the acetal in a substitution reaction, thereby resulting in a glycol monoether in which the R group of the ether moiety corresponds to the R group of the alcohol solvent.

This reaction may be illustrated by the following equation:

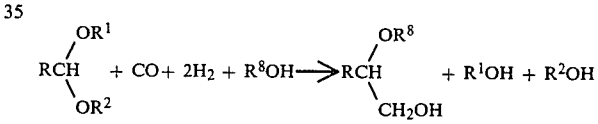

wherein R, $R^1$, and $R^2$ are as defined above except that cyclic acetals are not included, and $R^8$ is a different alkyl, cycloalkyl, or aryl group than $R^1$ and/or $R^2$, and desirably has from 1 to about 20 carbon atoms. Depending upon the length of time the reaction is allowed to continue, intermediate mixtures of higher and lower molecular weight substituents on the acetal corresponding to both those of the $R^1$ and/or $R^2$ groups and those of the alcohol solvent will be found in the reaction product.

The acetal starting materials employed in this invention have the aforedescribed general formula, namely

wherein R, $R^1$ and $R^2$ are as defined above. These acetals can be prepared in a known manner, separately or in situ, as for example as described in E. V. Dehmlav and J. Schmidt, Tetrahedron Letters, p.95–6 (1976) B. S. Bal and H. W. Pinnick, J. Org. Chem. V44 (21), p. 3727–8(1979) D. W. Hall, U.S. Pat. No. 3,492,356, Jan. 27 (1970), by the reaction of an aldehyde such as formaldehyde with an alcohol, or mixture of alcohols, of the general formula $R^1OH$ or $R^2OH$, where again $R^1$ and $R^2$ are as defined above, to form the corresponding acetal. In the case of cyclic acetals, the alcohol must be a diol. Hereinafter, when the acetal is referred to, it will be understood that the corresponding precursors, i.e., the desired aldehyde and alcohol, are also intended to be included.

As mentioned above, the $R^1$ and $R^2$ substituents of the acetal may comprise a bridging group to form such cyclic acetals as

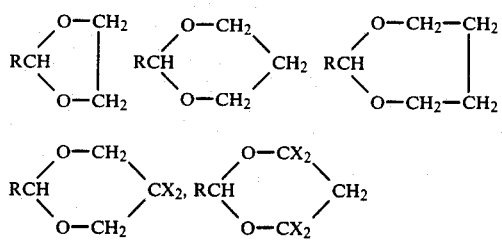

and the like, wherein R is as defined above, and X is selected from the group consisting of alkyl, aralkyl, aryl and cycloalkyl groups preferably those having from 1 to about 20 carbon atoms. As described above, cleavage of the ring under the conditions of this reaction will result in the formation of the corresponding hydroxy-substituted glycol ether.

Illustrations of products thus formed from cyclic acetals include, for example, diethylene glycol from dioxolane, the conversion of 2- or 4-methyldioxolane to the corresponding hydroxy glycol ether, and the like.

It is important in selecting the acetal starting material, that it not contain any substituents which would adversely affect the reaction. In other words, the R, $R^1$ and $R^2$ groups should not, for example, contain such reactive moieties as phosphine, arsine, amino, sulfido or carbonyl groups, acetal moieties, or olefins or acetylenic triple bonds. Other like groups will be recognized or readily determined by those skilled in the art as resulting in products other than the desired monoethers. On the other hand, halogen, alkoxy, and hydroxy moieties and the like may be present on the hydrocarbon substituents without adverse effect.

When these acetals are dealkoxyhydroxymethylated with syngas in accordance with the process of this invention, there is obtained the corresponding glycol monoether in which the ether moiety will correspond to the $R^1$ and $R^2$ groups of the acetal starting material. Also formed in lesser amounts are a tri-substituted ethane of the general formula

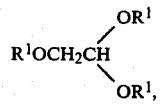

wherein $R^1$ (or, alternatively, $R^2$, or mixtures of $R^1$ and $R^2$) is as defined above, which may be recycled to form additional acetal starting material and alcohol by-products. Again, as above, if the $R^1$ and $R^2$ groups of the acetal are different, a mixture of corresponding R-substituted compounds will result. This tri-substituted ethane is believed to form during the reaction from an alkoxyacetaldehyde, e.g., the intermediate methoxyacetaldehyde, when methylal is used, ethoxyacetaldehyde when ethylal is used, and the like.

As shown below, the selectivities for the desired monoether over the tri-substituted by-product are in the ratio of from about 3:1 to as much as 10:1 or more.

In a preferred embodiment of this invention, the starting materials are preferably symmetrical acetals where the $R^1$ and $R^2$ groups are lower alkyl groups of 1 to about 4 carbon atoms, thereby forming the corresponding glycol mono-lower alkyl ethers such as the monomethyl ether, the monoethyl ether, and the like.

Alternatively, the acetal may contain such $R^1$ and $R^2$ groups as naphthyl and phenyl. In the case of naphthyl, the reaction of, e.g., the formaldehyde acetal with syngas will provide 2-(2-naphthyloxy) ethanol, a known sedative, which in turn may be oxidized to the corresponding 2-naphthyloxyacetic acid, a plant growth hormone.

Likewise, the dealkoxyhydroxymethylation of the, e.g., formaldehyde acetal wherein $R^1$ and $R^2$ are phenyl, will produce 2-phenoxy-ethanol, a topical antiseptic, which when oxidized, results in phenoxyacetic acid, a fungicide. Similarly, the formaldehyde acetal, wherein $R^1$ and $R^2$ are 2,4, 5-trichlorophenyl will yield, 2, 4, 5-trichlorophenoxyacetic acid, an herbicide. In a like manner, when $R^1$ and $R^2$ are p-nonylphenyl, p-nonylphenoxyacetic acid, a corrosion inhibitor and antifoaming agent in gasoline and cutting oils will be formed.

Each of these aforedescribed products may be recovered routinely by methods well known in the art.

The invention will now be illustrated by, but is not intended to be limited to, the following examples.

EXAMPLES

EXAMPLES 1-7

A series of runs was carried out in which the following general procedure was employed, using as the catalyst $Co_2Ru(CO)_{11}$, as well as mixtures of $Co_2(CO)_8$ and $Ru_3(CO)_{12}$, or $Co_2(CO)_8$ alone for comparative purposes:

To a 300 ml stainless steel autoclave equipped with a magnedrive stirrer was charged: methylal, solvent and catalyst. Carbon monoxide and hydrogen were admitted and the reaction mixture was rapidly heated to the desired temperature. The mixture was stirred for the designated time at reaction temperature after which the reactor was cooled by immersion in an ice bath. When the contents reached 25° C. the final pressure was recorded. After venting the gas the liquid was analyzed by GLPC.

The results are reported in Table I below. The specific reaction conditions, amounts, and solvent are as described in footnote (a) in this table.

TABLE I

METHYLAL DEALKOXYHYDROXYMETHYLATION[a]

| Examples | Catalyst Used, mmoles | | | GC Analysis of Reaction Mixture (Wt. %) | | | | Conv. Wt. % | Wt. % EGMME[b] In Product[d] |
|---|---|---|---|---|---|---|---|---|---|
| | [Co$_2$(CO)$_8$] | [Ru$_3$(CO)$_{12}$] | [RuCo$_2$(CO)$_{11}$] | CH$_2$(OCH$_3$)$_2$ | CH$_3$OH | EGMME[b] | OTHERS[c] | | |
| 1 | 5 | 0 | 0 | 25 | 42 | 18 | 15 | 75 | 24 |
| 2 | 5 | 5 | 0 | 29 | 33 | 30 | 8 | 71 | 42 |
| 3 | 3 | 0 | 0 | 33 | 33 | 17 | 17 | 67 | 25 |
| 4 | 3 | 1 | 0 | 37 | 26 | 25 | 12 | 63 | 40 |
| 5 | 3 | 3 | 0 | 38 | 30 | 25 | 7 | 62 | 40 |

TABLE I-continued

| | | METHYLAL DEALKOXYHYDROXYMETHYLATION[a] | | | | | | | |
|---|---|---|---|---|---|---|---|---|---|
| Exam- | Catalyst Used, mmoles | | | GC Analysis of Reaction Mixture (Wt. %) | | | | Conv. | Wt. % EGMME[b] |
| ples | [Co$_2$(CO)$_8$] | [Ru$_3$(CO)$_{12}$] | [RuCo$_2$(CO)$_{11}$] | CH$_2$(OCH$_3$)$_2$ | CH$_3$OH | EGMME[b] | OTHERS[c] | Wt. % | In Product[d] |
| 6 | 0 | 0 | 3 | 36 | 31 | 22 | 11 | 64 | 34 |
| 7 | 0 | 0 | 3 | 36 | 29 | 24 | 11 | 64 | 38 |

[a]A mole of methylal, .094 moles of toluene, an the catalyst(s) were pressured to 2400 psig with a 2/1 mixture of H$_2$/CO and heated for 2-3 hrs. at 150° C. The reaction mixture was analyzed by GC.
[b]EGGME = CH$_3$OCH$_2$CH$_2$OH + related C$_2$ products (i.e., CH$_3$OCH$_2$CH(OCH$_3$)$_2$)
[c]Others = CH$_3$OCH$_3$, CH$_3$CH$_2$OH and heavy by-products
[d][EGGME/(CH$_3$)H + EGGME + Others)] × 100

EXAMPLE 8

To a 110 ml. rocking autoclave are charged Co$_2$Ru(CO)$_{11}$, (0.75 mmoles); methylal (70.6 mmoles); and o-dichlorobenzene, (23.55 gms). After flushing thoroughly with ½ (CO:H$_2$) syngas, 800 psig of CO is admitted, then hydrogen to a total pressure of 2400 psig. The autoclave is rocked at 150° C. for 3 hours, then cooled, the product removed and analyzed by standardizing GLPC. A high yield of ethylene glycol monomethyl ether is obtained.

EXAMPLE 9

Using the procedures of Example 8, but substituting diethoxymethane for methylal, a good yield of ethylene glycol monoethyl ether is obtained.

EXAMPLE 10

Using the procedures of Example 8, but substituting dibutoxymethane for methylal, an excellent yield of ethylene glycol monobutyl ether is obtained.

EXAMPLE 11

Using the procedures of Example 8, but substituing 0.4 mmoles of paraformaldehyde for methylal, and 25 grams of butanol for o-dichlorobenzene, a good yield of ethylene glycol monobutyl ether is obtained.

EXAMPLE 12

Using the procedure of Example 8 but substituting diethoxyethane for methylal, propylene glycol monoethyl ether is the major reaction product.

EXAMPLE 13

To a 110 ml. rocking autoclave is charged Co$_2$Ru(CO)$_{11}$ (0.75 mmoles); methylal (27 mmole), butanol (18.5 ml.), and mesitylene as an internal standard. Carbon monoxide, 800 psig, is added and hydrogen added to a total pressure of 3200 psig. The mixture is rocked at 150° C. for six hours, cooled and analyzed by standardized glpc. A good yield of the monobutylether of ethylene glycol is produced.

EXAMPLE 14

In accordance with the procedures of Example 2, except that the cyclic acetal, dioxolane, is used instead of methylal, diethylene glycol is produced as a reaction product.

What we claim is:

1. Process for the dealkoxyhydroxymethylation of an aldehyde acetal of the formula

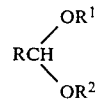

wherein R is hydrogen, alkyl, cycloalkyl, or aryl; r$^1$ and r$^2$, which may be same or different, are alkyl, cycloalkyl, or aryl, and wherein R$^1$ and R$^2$, taken together, may form a cyclic acetal, which comprises reacting said acetal, which has been formed separately or in situ, with syngas in the presence of a catalytically effective amount of a catalyst comprising the complex Co$_2$Ru(CO)$_{11}$ to form the corresponding glycol monoether.

2. Process of claim 1 wherein the temperature is in the range of from about 100° to 200° C.

3. Process of claim 1 wherein the pressure is in the range of from about 500 to 5000 psi.

4. Process of claim 1 further comprising carrying out the reaction in the presence of an inert organic solvent.

5. Process of claim 4 wherein the inert organic solvent is a chlorinated aromatic solvent.

6. Process of claim 5 wherein the chlorinated aromatic solvent is chlorobenzene or dichlorobenzene.

7. Process of claim 1 wherein R$^1$ and R$^2$ are alkyl groups having from 1 to 20 carbon atoms.

8. Process of claim 7 wherein the alkyl groups are lower alkyl.

9. Process of claim 1 wherein the weight ratio of catalyst to acetal, in grams, is in the range of from about 1:100-10:1.

10. Process of claim 1 wherein R is hydrogen, and the product is an ethylene glycol monoether.

11. Process of claim 1 wherein R is methyl, and the product is a propylene glycol monoether.

12. Process of claim 1 wherein R is ethyl, and the product is a butylene glycol monoether.

13. Process of claim 1 further comprising reacting the acyclic acetal in the presence of an excess of an alcohol solvent of the formula

R$^8$OH wherein R$^8$ is an alkyl, cycloalkyl, or aryl, and wherein R$^8$ is different than either the R$^1$ or R$^2$ group of the acetal starting material, or both, to form a glycol ether of the formula

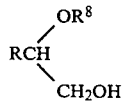

wherein R and R$^8$ are as defined above.

14. The process of claim 13 wherein R$^8$ is lower alkyl.

15. Process of any of claims 1-14 wherein the volume ratio of carbon monoxide to hydrogen in the syngas is in the range of from about 1:5 to 5:1.

16. Process of any of claims 1-14 wherein the volume ratio of carbon monoxide to hydrogen in the syngas is in the range of from about 1:3 to 3:1.

* * * * *